United States Patent [19]

Kay et al.

[11] Patent Number: 4,743,231
[45] Date of Patent: May 10, 1988

[54] DRUG ADMINISTRATION NEEDLE UNIT

[75] Inventors: Donald A. Kay, Sharon; Per Troein, Foxboro, both of Mass.

[73] Assignee: Pharmacia Nutech, Walpole, Mass.

[21] Appl. No.: 70,172

[22] Filed: Jul. 6, 1987

[51] Int. Cl.[4] .............................................. H61M 5/00
[52] U.S. Cl. .................................... 604/180; 604/177;
128/DIG. 26
[58] Field of Search ............... 604/181, 180, 177, 174, 604/117, 272; 128/DIG. 26

[56] References Cited
U.S. PATENT DOCUMENTS

| | | | |
|---|---|---|---|
| 4,235,234 | 11/1980 | Whitney et al. | 604/117 |
| 4,633,863 | 1/1987 | Filips et al. | 604/180 |
| 4,645,495 | 2/1987 | Vaillancourt | 604/180 |

*Primary Examiner*—Stephen C. Pellegrino
*Attorney, Agent, or Firm*—Cesari and McKenna

[57] ABSTRACT

A needle or cannula set especially adapted to access an implanted drug delivery portal includes a rigid base having a flat undersurface and a low profile. The base supports one end of a needle so that the needle projects from the base perpendicular to the base undersurface. One end of a flexible tube is secured to the base in fluid communication with the needle and the opposite end of the tube is terminated by a connector. A complaint pad is mounted to the base undersurface to assure proper seating of the base against the skin of the patient when the needle unit is inserted in the patient. The set also includes a handle which releasably connects to the base to facilitate inserting the needle unit into and withdrawing it from the patient and an adhesive dressing which is arranged to drape over the base with its edge margin extending all around the base for anchoring the needle unit to the patient and for providing an occlusive seal all around the puncture site. The set may also include a needle cover releasably coupled to the base to protectively enclose the needle and compliant pad prior to using the needle unit.

11 Claims, 1 Drawing Sheet

DRUG ADMINISTRATION NEEDLE UNIT

This invention relates to a needle unit suitable for administering a drug or other infusate to a patient over a relatively long period of time. It relates more specifically to a needle or cannula unit for injecting a drug percutaneously into an implanted drug delivery portal having an outlet catheter which leads to an infusion site in the patient's body.

BACKGROUND OF THE INVENTION

When a drug must be administered to a patient over a relatively long period of time, a common procedure is to implant a drug administration portal just under the skin at a convenient location in the patient's body. The portal, an example of which is marketed by Pharmacea Inc. under its PORT-A-CATH trademark, is basically a small chamber with an outlet tube or catheter leading to a selected infusion site in the body. The portal also has an inlet passage into the chamber fitted with a needle-penetrable, self-sealing septum. When the portal is implanted, the septum is situated just under the skin so that infusate can be introduced into the portal chamber by inserting a needle or cannula connected to an infusate source, e.g. a syringe, through the patient's skin and the septum into the inlet passage.

The portal is usually implanted so that its septum is more or less parallel to the skin surface necessitating a needle penetration at a 90 degree angle to the skin. Whereas the needles commonly used to administer drugs are straight non-coring-type needles, the needles used in this application are generally modified to have a 90 degree bend approximately one-half centimeter from the needle hub to assure a 90 degree skin penetration. This configuration permits easier manipulation of the hub in order to connect the hub to a syringe or extension set which connection is usually made parallel to the patient's skin. It also facilitates taping down of the needle and associated extension to the patient and provides a lower profile which is important if the needle is to be left in place for a long period of time under the patient's clothing.

While the 90 degree-bent needle provides greater ease of use and is an improvement over a standard straight needle, it is still relatively awkward to hold when the needle is being pushed through the portal septum against the resistance presented by the septum. Also, needles with a 90 degree bend are difficult to tape down so as to provide a sterile, sealed area all around the needle exit site from the body. Still further, the profile of the needle with its hub is not particularly smooth and often not close enough to the skin because the needle point "bottoms" in the portal while the needle hub is still spaced appreciably from the patient's skin. This type of variation occurs because conventional 90 degree-bent needles are made in discrete lengths and the position of the portal under the skin may vary due to factors such as the patient's size and weight. Resultantly, when the patient moves, there is often relative movement between the needle and the patient which, over a period of time, can cause considerably discomfort to the patient and can increase the risk of infection at the penetration site of the needle.

Finally, as these prior needles are difficult to insert into the patient, they are also awkward to remove from the patient due to the inability of the physician to firmly grasp the needle in order to withdraw it from the portal and the patient.

Over the past few years various support and guide devices have been developed to facilitate the insertion and maintenance in the body of needles, catheters, and cannulas. Examples of such devices are disclosed in U.S. Pat. Nos. 4,397,641; 4,435,174; and 4,569,675. Invariably, however, these devices are used in conjunction with standard needles and catheters in an attempt to adapt same to meet this particular application. As far as applicants are aware, there has been no attempt to design a drug administration needle or cannula specially adapted to access implanted drug administration portals.

SUMMARY OF THE INVENTION

It is an object of the present invention to provide a drug administration needle or cannula unit which is specially suited to access an implanted drug administration portal.

Another object of the invention is to provide a drug administration needle unit which is easy to insert into and withdraw from the patient.

A further object of the invention is to provide such a needle unit which is easy to secure firmly and reliably to the patient and which, when secured, has a low profile for wearability.

Yet another object of the invention is to provide a drug administration needle which provides a sterile seal over the needle and all around the puncture site in the patient.

Another object of the invention is to provide a disposable drug administration needle set, in the nature of a kit, whose components are packaged in a completely sterile environment prior to use.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly, our needle set comprises four separate components which are most desirably sold together in a package as a disposable sterile kit. All of these components are made of materials which are biocompatible and able to withstand normal ethylene oxide gas sterilization.

The first component of the set is a needle unit which includes a rigid base having an undersurface which defines a base plane. The base supports a needle or cannula at its center which needle projects down perpendicular to the base plane and is terminated by a Huber-type point or tip. The upper end of the needle or cannula is connected by way of the base to one end of a flexible tube whose opposite end is terminated by a standard Luer-lock connector. Secured to the underside of the base at the base plane so that it extends all around the needle is a compliant pad. The pad may be filled with antibiotic cream or antiseptic solution.

The second component of the needle set or kit is a handle which releasably attaches to the top of the base. The handle enables the physician to grasp and manipulate the needle unit when the needle is being inserted into and withdrawn from the patient. When the needle unit is in place in the patient, the handle is removed from the base to lower the base profile.

The third component of the needle set is a rigid cup-like cover which is arranged to clip to the underside of the needle base so that it protectively encloses the needle and the compliant pad supported by the base.

The fourth and final component of the needle set is a sterile adhesive dressing or patch which is specially shaped to drape over the needle base and to extend beyond the edge of the base so that it can be adhered to the patient's skin all around the puncture site. It thus secures the needle unit to the patient and provides a sterile seal all around the needle to minimize the likelihood of infection.

Prior to use, the needle unit, handle and cover are preferably connected together and maintained in a sterile condition within an hermetically sealed package along with the separate sterile dressing. To use the set, the physician opens the package and grasps the needle unit by the handle. The set is typically primed with normal saline. After separating the protective cover from the base, the physician inserts the needle through the patient's skin into the underlying implanted portal until the base's compliant pad seats against the patient's skin. That pad provides cushioning for increased comfort when the needle is taped down to the skin. Also, being compliant, the pad compensates for bumps, curves and other irregularities in the patient's skin where the needle base rests on the patient or when the needle has bottomed in the underlying portal. Since the pad completely fills the space between the base perimeter and the patient's skin, it also performs an asthetic or cosmetic function. Finally, the pad absorbs, and helps to confine the antibiotic cream that is generally applied to the puncture site.

After the needle unit is inserted, the handle is removed from the base and then the sterile adhesive dressing is draped over the base. A clearance hole is provided through the center of the dressing so that the dressing will lie flat against the top of the needle base, with the flexible tube attached to the base extending through that opening. The dressing substantially completely covers the base, with the edge margin of the dressing extending beyond the perimeter of the base so that the dressing can be adhered to the patient's skin all around the needle puncture site. Such adhesion not only secures the needle unit to the patient, it also provides a sterile seal over and all around the base so that the skin area around the puncture site is maintained in a completely sterile condition.

When the needle unit is secured to the patient in this fashion, the base and the needle supported thereby are very stable so that there is no relative movement between the needle and the patient when the patient moves. The flat shape of the needle base gives the overall device a very low profile so that there is minimal likelihood of the device being snagged by the patient's clothing as he or she moves or tosses about in bed. Therefore, discomfort to the patient is kept to a minimum.

Finally, the needle unit is connected to a syringe or other infusate source simply by coupling the Luer-lock connector attached to the free end of the tubing extending from the unit to a mating fitting leading from the infusate source.

When it becomes appropriate to remove the needle unit from the patient, the tubing is disconnected from the infusate source and the handle is reattached to the base. Then the physician strips the adhesive dressing away from the patient's skin while lifting up the handle until the needle is withdrawn from the patient. Since the physician can obtain a good grip on the handle, the needle unit can be withdrawn very quickly with minimum discomfort to the patient. After such use, all of the components of the needle set are thrown away.

BRIEF DESCRIPTION OF THE DRAWING

For a fuller understanding of the nature and objects of the invention, reference should be had to the following detailed description, taken in connection with the accompanying drawing, in which.

DESCRIPTION OF THE PREFERRED EMBODIMENT

Figure 1:
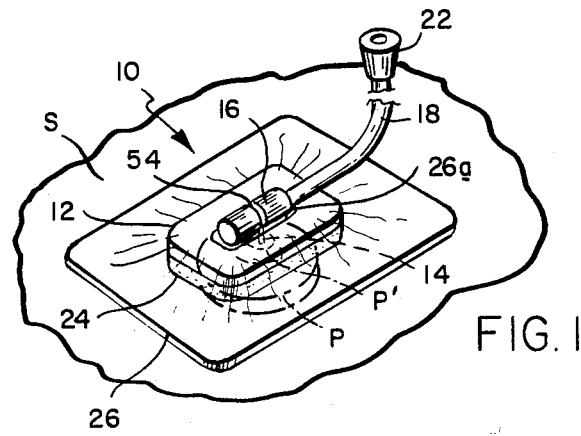
FIG. 1 is an isometric view of a drug administration needle unit embodying the invention.

Referring to FIG. 1 of the drawing, the drug administration needle unit shown generally at 10 is specially designed to introduce a drug into a drug delivery portal P implanted in a patient's body by penetrating the portal's self-sealing septum P' which is located directly under the patient's skin S, generally parallel to the skin plane.

As seen from FIG. 1, the needle unit 10 comprises a rigid base 12 which supports the upper end of a needle 14 which, in use, projects down from the base through the patient's skin S and through the portal septum P' so that the open needle tip or end 14a (FIG. 3) is located inside the portal P. Base 12 is molded of a clear biocompatible plastic material and includes a raised boss 16 into which extends one end of a length of flexible tubing 18, with the tubing being in fluid communication with needle 14. Preferably, boss 16 is cylindrical with its axis perpendicular to needle 14 so that it presents a rounded surface at the top of the base. The opposite end of tubing 18 is terminated by a conventional fitting such as a female Luer-lock connector 22. That connector is arranged to be releasably coupled to a mating connector (not shown) on the end of a tube leading from a conventional infusate source.

Secured to the underside of base 12 at least at the periphery thereof is a compliant pad 24 which, when needle unit 10 is inserted in the body, accommodates any irregularities or curves in the underlying skin area and completely fills the space between the base 12 perimeter and the patient's skin S. Base 12 is held securely against the patient's skin S by a sterile adhesive dressing or patch 26. The dressing has a central opening 26a to provide clearance for boss 16 so that the dressing can be placed flush against base 12 below tubing 18 with the edge margins of the dressing extending appreciably beyond the base perimeter so that the adhesive underside 26b (FIG. 3) of the dressing can be adhered to the patient's skin S over a relatively large annular area beyond the periphery of base 12.

When adhered to the body in this fashion, dressing 26 prevents movement of base 12 and its needle 14 relative to the patient. The dressing also provides an occlusive seal above and all around base 12 and the needle penetration site. Due to the presence of the compliant pad 24 between base 12 and the skin S, the needle can be worn by the patient for a relatively long time with little discomfort. Patient discomfort is minimized also because the needle unit 10 only projects a small distance above the patient's skin, i.e. it has a low profile. Therefore, the needle unit can be worn comfortably under the patient's clothing.

Figure 2:
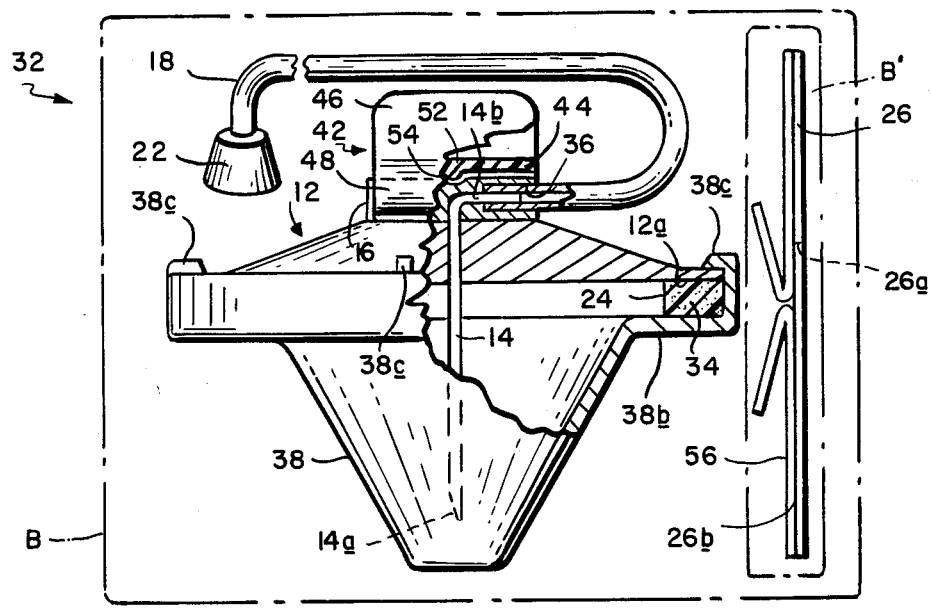
FIG. 2 is an elevational view on a larger scale with parts cut away showing in greater detail the components of a needle set including the FIG. 1 unit.

Refer now to FIG. 2 which shows needle unit 10 in greater detail. Preferably it is sold or distributed as part of a needle set or kit shown generally at 32, with all of the kit components being contained inside a sterile, package or bag B. As seen from that figure, base 12 has a profile that is generally frustoconical. The undersurface of the base, at least at the edge margin 12a thereof, is flat and defines a base plane. Pad 24, in the form of a ring of open cell foam material, is adhered to surface 12a. The pad can be supplied permeated by a standard antiseptic or antibiotic solution or cream indicated by stippling at 34 in FIG. 2.

The upper end 14b of needle 14 is bent at a right angle with respect to the needle axis and it is molded into base 12 and boss 16 so that the needle end 14b extends along the boss axis, with the remaining length of the needle projecting down perpendicular to the base undersurface margin 12a. Typically needle 14 is made of stainless steel and is about one inch long. Its tip 14a is preferably of the non-coring type.

A passage 36 extends in from the end of the base boss 16 that faces needle upper end 14b and the adjacent end of tubing 18 is inserted into passage 36 with the needle end 14b projecting into the tubing lumen. The tubing end may be secured in place within the boss by an appropriate cement or bonding agent so that there is a fluid-tight connection between the tubing and the needle upper end 14b.

Still referring to FIG. 2, the needle set 32 also includes a rigid protective cover 38 for needle 14. Cover 38 is molded of a medical grade plastic and it has a more or less frustoconical shape that can accommodate the length of needle 14 with some room to spare. The rim of the cover is shaped and dimensioned similar to base 12 so that the rim can be engaged around the edge of the base. Also, a peripheral ledge 38b is formed adjacent to the cover rim to provide clearance for pad 24 at the underside of base 12 when the cover is attached to the base as shown. A set of upwardly extending resilient clips 38c are spaced around the cover rim 38a which, when the cover is positioned against the underside of base 12 as shown in FIG. 2, releasably engage the edge of the base thereby securely retaining the cover against the base. When clipped to the base as shown, the cover 38 protectively encloses needle 14 and pad 24.

Figure 3:
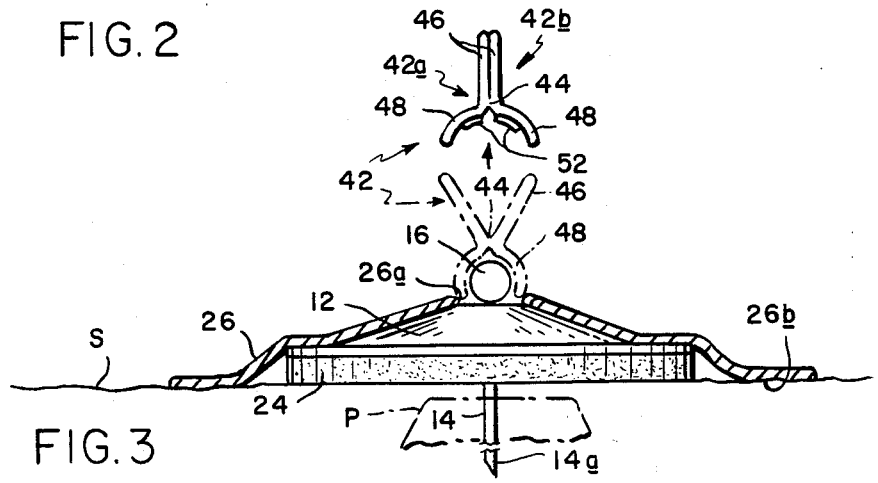
FIG. 3 is an end view illustrating the use of the needle unit.

The needle set 32 includes, in addition, a handle 42 which facilitates inserting needle 14 into and withdrawing it from the patient. Handle 42 is a unitary part that is molded of a medical grade plastic material. The handle 42 specifically depicted in FIGS. 2 and 3 is composed of two mirror-image sections 42a and 42b which are connected together along their length by a living hinge 44 to form a clip. The handle sections 42a and 42b have the same length as the plate boss 16 and each includes a generally rectangular upper tab or ear 46 and a generally semicylindrical arm 48 whose diameter corresponds to that of boss 16. The handle arms 48 are dimensioned and shaped so that when the handle is relaxed, those arms will clip tightly around boss 16 as shown in FIG. 2 and in phantom lines in FIG. 3. Preferably, the handle includes a pair of arcuate ribs 52 at the undersides of arms 48 which ribs engage in a circumferential groove 54 (FIG. 1) in boss 16 to center the handle 42 along the boss. When the tabs or ears 46 are pressed together as shown in solid lines in FIG. 3, the handle sections pivot at hinge 44 so that the arms 48 spread apart allowing the handle to be removed from boss 16. Normally, when the needle set is in its package B, handle 42 and cover 38 are clipped to the needle base 12 as shown in FIG. 2.

Still referring to FIG. 2, the needle set 32 also includes in a separate B' package at least one sterile dressing 26. The dressing can be made of any standard material such as gauze or tape and preferably it is transparent as shown in FIG. 1 so that when the needle unit 10 is worn by the patient, the skin area around base 12 can be examined for signs of possible infection. As noted above, dressing 26 has a central opening 26a to provide clearance for tubing 18 and base boss 16 and preferably strippable backing strips 56 cover and protect the adhesive surface 26b of the dressing until the dressing is used.

Referring now to FIGS. 2 and 3, to use the needle set 32, the set components are removed from bag B and the needle cover 38 is detached from base 12. Then, the physician manipulates the needle unit 10 using the attached handle 42 to position needle point 14a against the patient's skin S directly above the portal septum P'. The physician then pushes base 12 toward the patient so that the needle tip penetrates the skin and portal septum. Assuming that the physician has selected a unit with a needle 14 of the proper length, when the needle tip 14a is positioned properly in portal P', the compliant pad 24 at the underside of base 12 will be positioned against the patient's skin S and be compressed slightly so that the pad will compensate for any irregularities in the underlying skin area as shown in FIG. 3.

When the needle base is seated thusly, pad 24 will provide a barrier all around the needle penetration or puncture site thereby containing the antiseptic material which the physician normally applies to that site. Pad 24 also completely fills the space between base 12 and the patient's skin area thereby lending stability to the needle unit and giving it a neat appearance which is desirable from a cosmetic standpoint. After the needle unit has been inserted, the physician can remove handle 42 by pinching the handle ears 46. This action spreads apart the handle arms 48 allowing the handle to be separated from the plate boss 16 as shown in solid lines in FIG. 3.

After the handle has been removed from boss 16, the needle unit 10 is secured in place by the sterile dressing 26 included in set 32. The connector 22 and then tubing 18 are threaded through the dressing opening 26a. The dressing is then positioned with its adhesive surface 26b facing the upper surface of base 12, with boss 16 projecting through dressing opening 26a as shown in FIG. 3. The backing strips 56 are then peeled away from the adhesive surface 26b of the dressing. The dressing 26 adheres to the base so that it completely covers the base leaving a relatively wide peripheral edge margin that can be adhered to the patient's skin area around the base. The physician can now couple connector 22 to a mating connector leading from an infusion source.

Thus, when the needle unit 10 is in place as shown on FIG. 3, dressing 26 provides a sterile, occlusive seal above and all around base 12 and needle 14 thereby minimizing the likelihood of infection at the site of needle penetration into the patient's body. The dressing also securely anchors base 12 to the patient so there is minimum movement of the needle unit 10 relative to the patient's body. That factor, coupled with the presence of the compliant pad 24, ensures that the patient will suffer relatively little discomfort even if the needle unit 10 must be worn for a long period of time. Such patient discomfort is minimized also because, as shown in FIG. 3, without handle 42, the inserted needle unit 10 has a very low profile. In fact, aside from tube 18, the only projecting part is the boss 16 and that is rounded as noted above. Therefore, there is minimum likelihood of the needle unit being snagged by the patient's clothing.

When it is time to remove the needle unit 10 from the patient, the physician simply re-clips handle 42 to the base boss 16 by squeezing the handle ears 46 together. Then he lifts the edge margin of dressing 26 that is adhered to the patient's skin area and withdraws the needle unit 10 from the patient's body. Because the physician can obtain a firm grip on the needle unit by way of handle 42, the needle 14 can be withdrawn from the patient very quickly and with minimum discomfort to the patient.

After decoupling connector 22 from its mate, the physician may then reattach cover 38 to base 12 to prevent the used needle 14 from injuring others and the entire unit 10 can be thrown away.

It will thus be seen that the objects set forth above, among those made apparent from the preceding description, are efficiently attained and, since certain changes may be made in the above construction without departing from the scope of the invention, it is intended that all matter contained in the above description or shown in the accompanying drawing be interpreted as illustrative and not in a limiting sense.

It is also to be understood that the following claims are intended to cover all of the generic and specific features of the invention herein described.

What is claimed as new and desired to be secured by Letters Patent of the United States is:

1. A drug administration needle or cannula set comprising
A. a rigid base having
   (1) an upper surface
   (2) a relatively flat smooth undersurface area, and
   (3) a low profile;
B. a tubular needle or cannula having one end that is pointed and an opposite end that is secured to the base at the middle thereof so that the needle projects from the base generally perpendicular to the base undersurface area;
C. a flexible tube having one end secured to the base in fluid communication with said opposite end of the needle or cannula;
D. a handle;
E. coacting means on the base upper surface and on the handle for releasably connecting the handle to the base; and
F. a sheetlike dressing, said dressing having
   (1) an adhesive surface,
   (2) an area that is appreciably larger than that of the base undersurface, and
   (3) means defining an opening in the dressing so that when the dressing is draped over the upper surface of the base with said flexible tubing projecting through said opening, the dressing lies flat against the base upper surface with a relatively wide annular edge margin of the dressing extending beyond the periphery of the base.

2. The set defined in claim 1 and further including a compliant pad mounted to the base undersurface areas and extending all around the base periphery.

3. The set defined in claim 2 wherein said pad is composed of an open-cell plastic foam material.

4. The set defined in claim 3 and further including an antiseptic or antibiotic cream permeating said foam material.

5. The set defined in claim 2 and further including a fluid connector mounted to the free end of said flexible tube.

6. The set defined in claim 2 wherein said dressing includes a backing releasably covering the adhesive surface of the dressing.

7. The set defined in claim 2 and further including a rigid dished cover having
A. a depth that is greater than the length of the segment of the needle that projects from the base;
B. a rim profile that permits the cover to be placed at the base undersurface so that the cover completely encloses the base undersurface, the needle and the compliant pad; and
C. means on the cover or the base for releasably coupling the cover to the base.

8. The set defined in claim 1 wherein said coacting means comprise
A. a boss projecting from the upper surface of the base; and
B. clip means on the handle which, by manipulating the handle, can be clipped to the boss.

9. The set defined in claim 8 wherein the boss is generally cylindrical with a longitudinal axis that extends perpendicular to the needle.

10. The set defined in claim 9 wherein said opposite end of the needle
A. is bent perpendicular to the segment of the needle that projects from said base;
B. extends along the longitudinal axis of the boss; and
C. is joined to said tubing end inside the boss.

11. The set defined in claim 8 wherein said handle comprises
A. a pair of mirror-image clip sections, each section including a tab and a clip arm, the latter being shaped to engage partially around the boss; and
B. resilient hinge means joining the two sections so that when the tabs are pressed together, the clip arms will spread apart, and when the tabs are released, the clip arms will spring together.

* * * * *